United States Patent [19]

Gallagher et al.

[11] Patent Number: 5,792,797

[45] Date of Patent: Aug. 11, 1998

[54] PHARMACEUTICAL COMPOUNDS

[75] Inventors: Peter Thaddeus Gallagher, Camberley; William Martin Owton, Lightwater; Andrew Caerwyn Williams, Camberley, all of United Kingdom

[73] Assignee: Lilly Industries Limited, Basingstoke, England

[21] Appl. No.: 805,960

[22] Filed: Feb. 25, 1997

Related U.S. Application Data

[62] Division of Ser. No. 518,447, Aug. 23, 1995, Pat. No. 5,668,172.

[30] Foreign Application Priority Data

Aug. 24, 1994 [GB] United Kingdom ............... 9417102

[51] Int. Cl.$^6$ ............................................. A61K 31/19
[52] U.S. Cl. ............................................. 514/569
[58] Field of Search ........................... 552/208; 514/569

[56] References Cited

U.S. PATENT DOCUMENTS

| | | | |
|---|---|---|---|
| 3,752,813 | 8/1973 | Shen et al. ........................ | 260/267 |
| 3,984,429 | 10/1976 | Peel et al. ........................ | 260/308 D |
| 3,984,534 | 10/1976 | Peel et al. ........................ | 424/45 |
| 4,226,784 | 10/1980 | Kalopissis et al. ................ | 260/378 |
| 4,244,968 | 1/1981 | Freidmann ........................ | 424/308 |
| 4,363,743 | 12/1982 | Moeller et al. ................... | 252/299.1 |
| 4,402,854 | 9/1983 | Gunther et al. ................... | 252/299.1 |
| 4,456,545 | 6/1984 | Weber et al. ..................... | 252/299.1 |
| 4,762,648 | 8/1988 | Stache et al. ..................... | 260/383 |
| 4,950,687 | 8/1990 | Dall'Asta et al. .................. | 514/548 |
| 4,966,918 | 10/1990 | Watanabe et al. .................. | 514/656 |
| 5,030,387 | 7/1991 | Matsuoka et al. .................. | 252/582 |
| 5,393,898 | 2/1995 | Carcasona et al. .................. | 552/262 |
| 5,480,873 | 1/1996 | Brunavs et al. .................... | 514/33 |

FOREIGN PATENT DOCUMENTS

| | | |
|---|---|---|
| 875-945 | 8/1979 | Belgium . |
| 0 243 968 | 11/1987 | European Pat. Off. . |
| 0 253 144 | 1/1988 | European Pat. Off. . |
| 0 454058A2 | 4/1991 | European Pat. Off. . |
| 2508 798 | 7/1991 | France . |
| 27 11 493 | 10/1977 | Germany . |
| 1278543 | 6/1972 | United Kingdom . |
| 92/10464 | 6/1992 | WIPO ............ C07C 69/96 |
| 92/16496 | 10/1992 | WIPO ............ C07C 235/66 |
| 92/19584 | 11/1992 | WIPO ............ C07C 69/95 |

OTHER PUBLICATIONS

Arai, et al., Amide Ion Formation and N–Alkylation of Aminoanthraquinones in the Presence of Potassium Hydroxide in Dimethyl Sulfoxide:, *Bull. Chem. Socl Japan* 58(5), 1458–1463 (1985).

Dreyfus, et al., Synthese de substances macromoleculaires renfermant des motifs monomeres derives de colorants:, *Bull. Soc. Chem. France*, 5–6 1196–1200 (1975).

Chemical Abstracts, 31: Abstract No. 3040(7), (1937).

Katzhendler, et al., Synthesis of aminoanthraquinone derivatives and their in vitro evaluation as potential anti–cancer drugs:, *Eur. J. Med. Chem.*, 24, 23–30 (1989).

Peters, et al., Structure–property relationships in 1,2,4–tridonor–substituted anthraquinones–2–amino–1,4–dihydroxyanthraquinones:, *J. Soc. Dyers Colour*, 105, 315–321 (1989).

Castle, et al., "The Synthesis of some Monomethylanthracenamines", *Cham. Abstr.*, 116:105789f (1992).

Sal'nikova, et al., "Substituted Amedic of 2–anthraquinone–succinamenic acid: Synthesis and Study of Their Pharmacological Activity", *Chem. Abstr.*, 113:204406 (1990).

Alemayehu, et al., "Quinones of Senna didymobotrya", *Chem. Abstr.*, 112:52218c (1990).

Horner, et al., "Corrosion Inhibitors 23(1)", *Chem, Abstr.*, 90:91154a (1979).

Metwally, Reaction of Hydroxymethylanthraquinones with Thionyl Chloride:, *J. Appl. Chem. Biotechnol.*, 25, 161–168 (1975).

Alexander, et al., "Methylation and Hydroxylation Studies on Aloe–emodin", *J. Org. Chem.*, 45,20–24, (1980).

Yamada, et al, "Electrophotographic Photoreceptor Using Disazo Compound Charge–generating Agent", *Chem. Abstr.*, 115:194178a (1991) of JP03 69,962.

Hayashi, et al., "Colored Rubbers and Rubber Additives", *Chem. Abstr.*, 113:25368r (1990).

Proter, Derwent Abstract 84–020099/04 of J5 8210–009–A.

Antonello, et al., "Diethylaminopropionamido–hydroxy–anthraquinones as Potential Anticancer Agents: Synthesis and Characterization", *Arch. Pharm.* (Weinheim), 322, 541–544 (1989).

Mosby, et al., "Products of Nucleophilic Displacement Reactions in the Anthraquinone Series", *Tetrahedron*, 8, 107–115 (1960).

Slavik, et al, "Substitution of NH Hydrogen in Nitrogen Derivatives of Polycyclic Hydrocarbons and Quinones", *Coll. Czech. Chem. Comm.*, 4 (40), 1193–1198 (1975).

(List continued on next page.)

*Primary Examiner*—James H. Reamer
*Attorney, Agent, or Firm*—Janelle D. Strode; James P. Leeds; David E. Boone

[57] ABSTRACT

A pharmaceutical compound of the formula

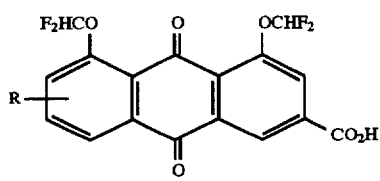

in which

R is hydrogen, halo or $F_2HCO$—;
or a salt, amide or ester thereof.

6 Claims, No Drawings

OTHER PUBLICATIONS

*Chemical Abstract*, 84, (6) Abstract No. 3257c, 78 (1976). Budziarek, Richard "The Reaction of Sodium Sulphite and Bisulphite with Nitro–and Hydroxylamino–Anthraquinones", *Chem, Ind.*, 15, 583–584 (1978).

*Chemical Abstracts*, 92, (1) Abstract No. 6302W, 592–593 (1980).

*Chemical Abstracts*, 95, (17) Abstract No. 150250g, 628 (1981).

Summers, et al., "Hydroxamic Acid Inhibitors of 5–Lipoxygenase: Quantitative Structure–Activity Relationships", *J. Med. Chem.*, 33 (3), 992–998 (1990).

*Beilsteins Handbuch der Organischen Chemie*, 4th Edition, 3rd Supplement 10, Part 5, 4787–4790 (1972).

PHARMACEUTICAL COMPOUNDS

This application is a division, of application Ser. No. 08/518,447 filed Aug. 23, 1995, now U.S. Pat. No. 5,608,172.

This invention relates to novel compounds and their use as pharmaceuticals.

The chemical literature describes many compounds derived from anthraquinone (9,10-dihydro-9,10-dioxoanthracene), for example, British Patent 1 578 452, which discloses compounds related to rhein (9,10-dihydro-4,5-dihydroxy-9,10-dioxoanthracene-2-carboxylic acid), a known compound.

The compounds of the invention have the following formula:

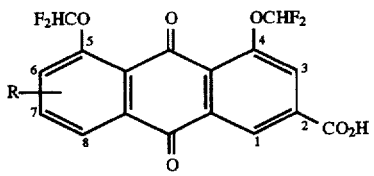

in which

R is hydrogen, halo or $F_2HCO$—;

or a salt, amide or ester thereof.

Such compounds are useful as pharmaceuticals. They modify cell function, and are indicated for use in the treatment of neuronal, cardiac and skeletal diseases, and also in the treatment of viral diseases, diabetes and associated complications of diabetes. In particular the compounds are indicated for treating rheumatoid arthritis, and connective tissue matrix diseases such as osteoarthritis and also cancer.

The compounds of the invention have increased stability by comparison with similar compounds which tend to metabolise readily by dealkylation to give rhein and related compounds.

In the above formula (I) halo can be fluorine, chlorine, bromine or iodine. Preferred compounds are those of formula (I) above in which R is in the 8-position, and a most preferred compound is of the formula:

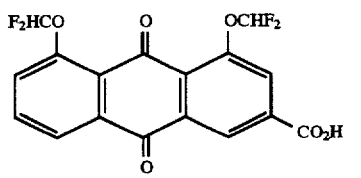

or a salt, amine or ester thereof. Preferred compounds are in the free acid or salt form.

The compounds of the invention can exist in salt form derived from any of the well known bases, such salts existing at the 2-carboxyl group. Preferably such salts are pharmaceutically-acceptable, but other salts are included as they may serve as intermediates in the purification of compounds or in the preparation of other salts, or are useful for identification, characterisation or purification. Examples are those derived from ammonium hydroxide and alkali and alkaline earth metal hydroxides, carbonates and bicarbonates, as well as salts derived from aliphatic and aromatic amines, aliphatic diamines and hydroxy alkylamines. Bases especially useful in the preparation of such salts include ammonium hydroxide, potassium carbonate, sodium bicarbonate, lithium hydroxide, calcium hydroxide, methylamine, diethylamine, ethylene diamine, cyclohexylamine and ethanolamine. The potassium, sodium and lithium salt forms are particularly preferred.

An amide is a compound with the substituent—$CONR^1R^2$, and includes substituents in which $R^1$ and $R^2$ are each hydrogen, alkyl such as $C_{1-4}$ alkyl or an amino acid residue, or together form an alkylene chain containing, for example, 4 to 6 carbon atoms. The amide is preferably a pharmaceutically-acceptable amide.

The compounds of the invention can also be utilised in ester form, for example, as an alkyl ester such as an ester of a $C_{1-4}$ alcohol or a benzyl ester in which the phenyl group is optionally substituted by one to three substituents selected from, for example, $C_{1-4}$ alkyl especially methyl, $C_{1-4}$ alkoxy especially methoxy, halo and nitro. The ester is preferably a pharmaceutically-acceptable ester.

The compound of formula (II) can be prepared by alkylation of the known compound, rhein, with chlorodifluoromethane, preferably at a temperature of from 50° C. to 250° C. and in an aqueous or organic solvent. Other compounds of formula (I) can be prepared, under similar conditions, by alkylation of an appropriately substituted rhein, such compounds being disclosed, for example, in Owton W. M. et al. J. Chem. Soc. Perkin Trans. 1, 1995, 931–934.

As mentioned above, the compounds are indicated for use in the treatment of osteoarthritis and allied connective tissue diseases such as, for example, osteoporosis and rheumatoid arthritis. Such diseases are often characterised by an increase in matrix synthesis and remodelling. Incorporation of newly synthesised components into a biological and biomechanically functional matrix is, however, frequently deficient. Drugs which modulate the activity of the cells involved in such connective tissue matrix maintenance and repair are, therefore, of potential use in such diseases.

Compounds of the invention produce dose-dependent inhibition of in vitro tumour cell proliferation. Partial inhibitory effects are observed on tumour cell protein synthesis at a concentration of 100 μM using a method similar to that described by A. Floridi et al, Exp. Mol. Pathol., 1985, 42, 293–305.

Further modulatory effects of the compounds of the invention are observed in an in vitro model system used to study the differentiation of chondrocytes from prechondrogenic stem cells, as described by D. F. Paulsen et al, In Vitro Cellular and Developmental Biology 24, 138–147.

Further evidence of activity is provided by studying the effect of the compounds on lesions in guinea pigs. Spontaneous lesions of osteoarthritis were first described in the hind knee joints of old guinea pigs by Silverstein and Sokoloff (Arthritis Rheum. 1, 82–86 (1958)). Bendele and Hulman (Arthritis Rheum. 31, 561–565 (1988)) and Bendele, White and Hulman (Lab. Anim. Sci. 39, 115–121 (1989)) studied younger animals and were the first to describe the time course of progressing osteoarthritis in outbred male guinea pigs. These latter studies were confirmed and extended by Meacock, Bodmer and Billingham (J. Exp. Path. 71, 279–293 (1990)), also in outbred male guinea pigs.

The compounds of the invention are thus indicated for use in the treatment of osteoarthritis and allied connective tissue matrix diseases such as, for example, osteoporosis and rheumatoid arthritis. Furthermore, the inhibitory properties on tumour cell proliferation indicate that the compounds are of potential in the treatment of cancer.

The invention also includes a pharmaceutical composition comprising a pharmaceutically acceptable diluent or carrier in association with a compound of the invention or a pharmaceutically acceptable salt or ester thereof.

The compounds may be administered by various routes, for example by the oral or rectal route, topically or parenterally, for example by injection or infusion, being usually employed in the form of a pharmaceutical composition. Such compositions are prepared in a manner well known in the pharmaceutical art and comprise at least one active compound. In making the compositions of the present invention, the active ingredient will usually be mixed with a carrier, or diluted by a carrier, and/or enclosed within a carrier which may, for example, be in the form of a capsule, sachet, paper or other container. When the carrier serves as a diluent, it may be a solid, semi-solid, or liquid material which acts as a vehicle, excipient or medium for the active ingredient. Thus, the composition may be in the form of tablets, lozenges, sachets, cachets, elixirs, suspensions, ointments containing, for example, up to 10% by weight of the compound, soft and hard gelatin capsules, suppositories, injection solutions and suspensions and sterile packaged powders.

Some examples of suitable carriers are lactose, dextrose, sucrose, sorbitol, mannitol, starches, gum acacia, calcium phosphate, alginates, tragacanth, gelatin, syrup, methyl cellulose, methyl- and propyl- hydrobenzoate, talc magnesium stearate and mineral oil. The compositions of the injection may, as is well known in the art, be formulated so as to provide quick, sustained or delayed release of the active ingredient after administration to the patient.

When the compositions are formulated in unit dosage form, it is preferred that each unit dosage form contains from 5 mg to 500 mg. The term 'unit dosage form' refers to physically discrete units suitable as unit dosages for human subjects and animals, each unit containing a predetermined quantity of active material calculated to produce the desired therapeutic effect, in association with the required pharmaceutical carrier.

The active compounds are effective over a wide dosage range and, for example, dosages per day will normally fall within the range of from 0.5 to 300 mg/kg, more usually in the range of from 5 to 100 mg/kg. However, it will be understood that the amount administered will be determined by the physician in the light of the relevant circumstances including the conditions to be treated, the choice of compound to be administered and the chosen route of administration, and therefore the above dosage ranges are not intended to limit the scope of the invention in any way.

The invention is illustrated by the following Examples.

EXAMPLE 1

Bis(difluoromethoxy)rhein [9,10-dihydro-4,5-bis (difluoromethoxy)-9,10-dioxoanthracene-2-carboxylic acid]

Rhein (3 g) was dissolved in water/dioxan (1:1) (150 ml). Sodium hydroxide pellets (5 g) were added and the reaction mixture was stirred and heated in an oil bath to a temperature of 65° C. Chlorodifluoromethane was bubbled into the reaction mixture at a rate such that no gas bubbled out. After 3 hours further sodium hydroxide pellets (3 g) were added, reaction continued with chlorodifluoromethane addition and the composition of the mixture was monitored by HPLC. After 10 hours the reaction mixture was poured into water. A yellow solid precipitated and was collected by filtration. This solid was dissolved in hot ethyl acetate. On cooling a yellow solid precipitated and was collected. This solid was purified by preparative scale HPLC to give the title compound which was characterised by ¹H N. M. R. (δ7.29(1H,t), 7.40(1H,t), 7.75(1H,dd), 7.95 (1H,t), 8.03(1H,d), 8.12(1H, dd), 8.50(1H,d), 11 (1H,broad).

EXAMPLE 2

Soft gelatin capsule
Each soft gelatin capsule contains:

| Active ingredient | 150 mg |
|---|---|
| Arachis oil | 150 mg |

After mixing together, the blend is filled into soft gelatin capsules using the appropriate equipment.

EXAMPLE 3

Hard gelatin capsule
Each active capsule contains:

| Active ingredient | 50 mg |
|---|---|
| PEG 4000 | 250 mg |

The PEG 4000 is melted and mixed with the active ingredient. Whilst still molten the mixture is filled into capsule shells and allowed to cool.

EXAMPLE 4

Tablets each containing 10 mg of active ingredient are made up as follows:

| Active ingredient | 10 mg |
|---|---|
| Starch | 160 mg |
| Microcrystalline cellulose | 100 mg |
| Polyvinylpyrrolidone (as 10% solution in water) | 13 mg |
| Sodium carboxymethyl starch | 14 mg |
| Magnesium stearate | 3 mg |
| Total | 300 mg |

The active ingredient, starch and cellulose are mixed thoroughly. The solution of polyvinylpyrrolidone is mixed with the resultant powders and passed through a sieve. The granules so produced are dried and re-passed through a sieve. The sodium carboxymethyl starch and magnesium stearate are then added to the granules which, after mixing, are compressed in a tablet machine to yield tablets each weighing 300 mg.

We claim:

1. A method of treating an animal, including a human, suffering from or susceptible to a skeletal disease, which comprises administering an effective amount of a compound of the formula

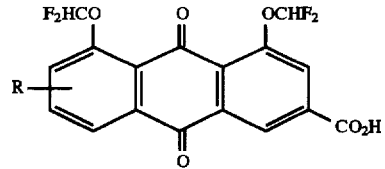

in which

R is hydrogen, halo or F2HCO—;

or a pharmaceutically-acceptable salt, amide, or ester thereof.

2. A method according to claim 1, wherein said skeletal disease is osteoarthritis.

3. A method according to claim 1, wherein said skeletal disease is osteoporosis.

4. A method of treating an animal, including a human, suffering from or susceptible to a neuronal disease which comprises administering an effective amount of a compound of the formula

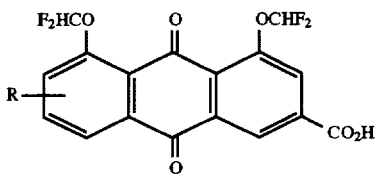

in which

R is hydrogen, halo or F2HCO—;
or a pharmaceutically-acceptable salt, amide, or ester thereof.

5. A method of treating an animal, including a human, suffering from or susceptible to a cardiac disease which comprises administering an effective amount of a compound of the formula

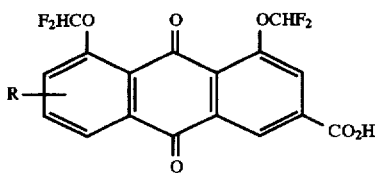

in which

R is hydrogen, halo or F2HCO—;

or a pharmaceutically-acceptable salt, amide, or ester thereof.

6. A method of treating an animal, including a human, suffering from or susceptible to tumor cell proliferation which comprises administering an effective amount of a compound of the formula

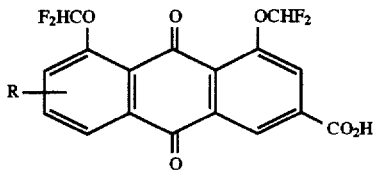

in which

R is hydrogen, halo or F2HCO—;

or a pharmaceutically-acceptable salt, amide, or ester thereof.

* * * * *